(12) United States Patent
Kaiser et al.

(10) Patent No.: US 7,420,183 B2
(45) Date of Patent: Sep. 2, 2008

(54) APPARATUS AND PROCESS FOR STERILIZATION OF LIQUID MEDIA BY MEANS OF UV IRRADIATION AND SHORT-TIME HEAT TREATMENT

(75) Inventors: Klaus Kaiser, Köln (DE); Jörg Kauling, Köln (DE); Hans-Jürgen Henzler, Solingen (DE); Sebastian Schmidt, Haan (DE); Franz Schmitt, Bergisch Gladbach (DE); Erhard Beckers, Burscheid (DE)

(73) Assignee: Bayer Technology Services GmbH, Leverkusen (DE)

( * ) Notice: Subject to any disclaimer, the term of this patent is extended or adjusted under 35 U.S.C. 154(b) by 481 days.

(21) Appl. No.: 10/801,746

(22) Filed: Mar. 15, 2004

(65) Prior Publication Data

US 2004/0248076 A1 Dec. 9, 2004

(30) Foreign Application Priority Data

Mar. 21, 2003 (DE) ................ 103 12 765

(51) Int. Cl.
*A61L 2/00* (2006.01)
(52) U.S. Cl. .................. 250/437; 250/435; 422/21; 422/22
(58) Field of Classification Search ......... 250/437, 250/436, 435, 432 R; 422/21, 22
See application file for complete search history.

(56) References Cited

U.S. PATENT DOCUMENTS

| 1,141,056 | A | | 5/1915 | Helbronner et al. |
| 3,926,556 | A | * | 12/1975 | Boucher .................. 422/21 |
| 3,934,042 | A | | 1/1976 | De Stoutz ................. 426/248 |
| 4,534,282 | A | | 8/1985 | Marinoza .................. 99/451 |
| 6,464,936 | B1 | * | 10/2002 | Mowat et al. .............. 422/22 |
| 2001/0051201 | A1 | | 12/2001 | Schubert et al. ........... 426/522 |
| 2002/0096648 | A1 | | 7/2002 | Kaiser et al. ............ 250/492.1 |
| 2003/0049809 | A1 | | 3/2003 | Kaiser et al. ............ 435/173.1 |
| 2003/0082072 | A1 | | 5/2003 | Koji et al. ................ 422/24 |

FOREIGN PATENT DOCUMENTS

| DE | 1 951 633 | 5/1971 |
| WO | WO 99/34910 | 7/1999 |
| WO | WO 00/56160 | 9/2000 |
| WO | WO 01/37675 A2 | 5/2001 |
| WO | WO 01/91811 A1 | 6/2001 |
| WO | WO 02/38502 A1 | 5/2002 |

* cited by examiner

*Primary Examiner*—Kiet T Nguyen
(74) *Attorney, Agent, or Firm*—Christa Hildebrand; Norris McLaughlin & Marcus, PA

(57) ABSTRACT

Apparatus and process for UV irradiation and heat sterilization of fluid media, and in particular of liquids containing microorganisms and/or viruses.

28 Claims, 8 Drawing Sheets

Fig.4
Fig.4a
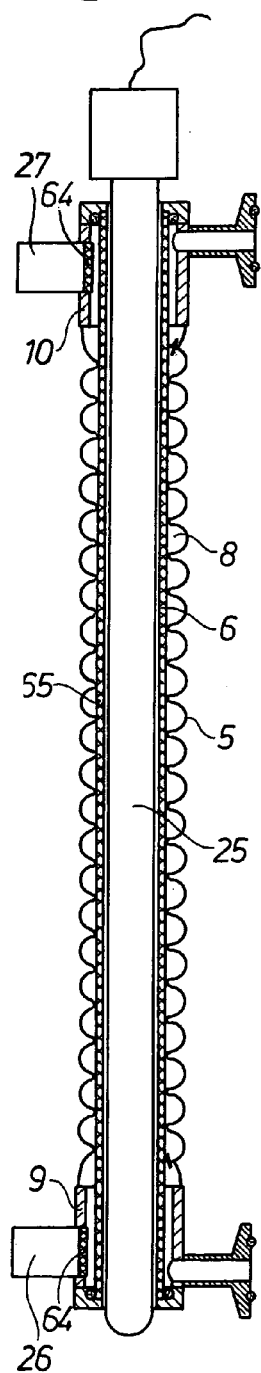
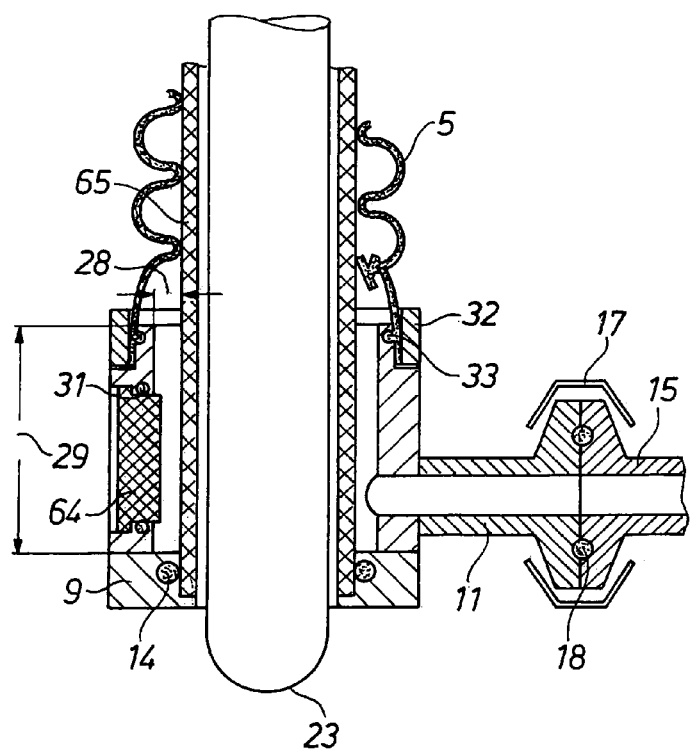

APPARATUS AND PROCESS FOR STERILIZATION OF LIQUID MEDIA BY MEANS OF UV IRRADIATION AND SHORT-TIME HEAT TREATMENT

This invention relates to a technique for reliable and product-saving UV irradiation and heat sterilization of fluid media, especially of liquids containing microorganisms and/or viruses (e.g. foodstuffs, milk products, fruit juice products, chemical or pharmaceutical products, viral vaccines, active substance or proteins produced by genetic engineering, active substances or proteins from transgenic animals or plants, and blood plasma, or products obtained from blood plasma). A common feature of irradiation with ultraviolet (UV) light and of treatment by heat is that the inactivation reaction is accompanied by undesired damage to the product, the extent of which damage must be minimized by means of suitable reaction techniques and structural measures.

The process of sterilization of fluid media is based on contemporaneous application of the two process steps of heat treatment and UVC (Ultraviolet radiation category C) treatment which, when used in combination, have synergistic effects which allow microorganisms and viruses to be killed in a manner which is particularly gentle on the product itself. The reactors used are helical flow channels with a limited dwell time spectrum for the product. The product channels are produced by drawing a spirally corrugated hose body onto a cylindrical pipe body which is heat transmitting and/or transparent to UV rays. To avoid cleaning which is difficult to validate, the helical reactors are constructed in such a way that, after the product has been treated, they can be replaced by new, precisely conditioned and sterilized reactors.

Sterilization of liquid media is an important precondition for the application of biotechnological production processes in the food industry and the pharmaceutical industry. The aim is to ensure reliable and extensive depletion of microorganisms and/or viruses while at the same time largely protecting the sensitive substances of value. The main areas of application of the sterilization processes are sterile fermentation operations, shelf-life extension by sterile or low-microbe packaging of foods, and the pharmaceutical suitability of biological active substances of human or animal origin, e.g. from organs or blood plasma. For the use of biological active substances, the FDA requires a sterilization process subject to validation and comprising several virus inactivation steps based on different principles of action. Validation of the sterilization processes requires that the reactors and installations used are in an exactly specifiable state. Cross contamination between process batches must be ruled out.

An important criterion in protecting the product involves minimizing the time during which the product is exposed in the reaction zone. Since the average duration of treatment needed is defined by the particles passing most quickly through the reaction zone, reducing the duration of treatment requires an as far as possible uniform dwell time distribution within the product stream. The literature [US 2002 096648 A1, US 2003 049809 A1, VDI heat atlas] describes the especially favorable dwell time behavior in helical flow channels, which is caused by secondary flows (so-called Dean vortices) acting perpendicular to the direction of flow (FIG. 3$b$, (23)) (24). As tests on inactivating a model virus have shown, it has been possible for the first time to obtain a uniform and precisely controllable treatment of product solutions. Each liquid element flowing through is guided into immediate proximity of the treatment source and thus exposed to the inactivating UV radiation or heat.

In addition to the improved through-flow, it has been found that the combination of the short-time heat treatment and UV treatment conducted under suitable conditions (temperature and UV irradiation dose) is particularly advantageous. By both process steps taking place in rapid succession (UV treatment of the product stream after heating and cooling, or UV treatment of the product stream before heating and cooling) or overlapping (heating of the product stream, UV treatment and cooling), an additional synergistic inactivation potential is induced. While giving the same inactivation success, this surprisingly leads to a reduction in the energy needed and thus to a decrease in product damage in the overall process. The application of the heat sterilization technique requires at least two reactors, one for the heating and one for the subsequent cooling. To keep the product temperature constant, a thermally insulated conduit can optionally be coupled in as a temperature-holding section between heating and cooling reactor. In the case of UV treatment being carried out within the thermal treatment, the UV reactor also serves as holding module.

SUMMARY OF THE INVENTION

The subject of the invention is a continuous process for sterilization and, if appropriate, virus inactivation of fluid media, in particular of aqueous reaction media, by means of a combined application of a heat treatment and a UV irradiation treatment, characterized in that the heat treatment of the fluid media (i.e., "product") takes place at a sterilization temperature of 400 to 135° C. and the irradiation takes place at an irradiation density of 5 to 300 W/m$^2$.

The fluid media (product) being treated is preferably held at the sterilization temperature for up to 50 seconds.

The heating of the fluid media to the sterilization temperature and the cooling of the fluid media take place independently of one another within 0.1 to 10 seconds.

A process is particularly preferred in which the thermal treatment takes place in successive steps of heating, temperature holding, and cooling (3), and the UV treatment takes place in particular during the thermal treatment.

The thermal treatment is preferably carried out using high-performance heat exchangers which, with a k value of k>1000 W/m$^2$*K, permit a heating and cooling of the product stream in a time of 0.1 to 10 seconds.

A process is further preferred in which all or some of the treatment steps are carried out using pre-sterilized disposable reactors cleaned according to GMP (Good Manufacturing Practice).

A further subject of the invention is an apparatus for carrying out the process according to the invention, and which is comprised of at least a heat treatment reactor, if appropriate a temperature-holding section, a UV irradiation reactor and a cooling reactor, characterized in that the sterilization and/or inactivation chamber through which the fluid media (product) flows, at least of the irradiation reactor and of the heat treatment reactor, is formed by a deformable, helical, profiled hollow cylinder which is drawn tight onto the wall of a rigid, straight, cylindrical support body transparent to the sterilization or inactivation energy used.

DETAILED DESCRIPTION

The deformable, helical hollow cylinder used is preferably a corrugated plastic hose which, for product delivery and discharge, is connected at both ends to distributor heads.

An apparatus is particularly preferred in which the distributor heads have tangential or preferably radial product delivery and discharge lines, free of dead space, in the area of the annular gap between distributor head and support pipe.

An apparatus is also preferred in which the distributor heads (9, 10) are worked from the hose ends by subsequent thermal deformation of the corrugated hose or are preferably made from a plastic material produced and worked by injection-molding and/or stretching, respectively, and are connected with a force fit to the cylindrically widened hose ends by means of an O-ring connection (32, 33) pressed on from the outside.

In a preferred embodiment, the corrugated hose has an outer jacket or a reinforcement for the connection.

The outer jacket is particularly preferably formed by a shrinkable plastic tube, a pipe pushed over the spiral hose, or preferably a two-part, cylindrical shell, the reinforcement being formed by a steel or plastic coil.

The UV irradiation reactor preferably has, as energy source, one or more UV emitters as energy source in the cylindrical support body, and the support body is preferably made of a material transparent to UV light, e.g. quartz glass, and if appropriate has a corrugated plastic hose.

An apparatus is further preferred in which windows (64) for observing the UV energy radiated into the product are formed in the distributor heads (9, 10), which windows (64) are sealed in the distributor heads (9, 10), in particular via an O-ring connection (31, 64).

In a particularly preferred design, UV sensors are built into the distributor heads for the purpose of detecting the UV radiation intensity radiated into the product chamber.

The heat treatment reactor particularly preferably has a pipe formed of a heat transmitting material, for example stainless steel, like 316L or V4A, Chromium-Nickel steels and austenitic steels, for the support pipe, and a corrugated hose made of plastic. Plastics useful for this purpose are Polytetrafluorethylene (PTFE), Perfluoroalkoxypolymers (PFA), FEP (Copolymers from Hexafluoropropylene and Tetrafluoroethylene), PVDF (Polyvinylidene fluorides), ECTFE as well as Polypropylenes and Polyethylenes.

In order to increase the heat transfer of a temperature control media flowing through the reactor, an insert element is preferably incorporated in the centre of the support pipe of the heat treatment reactor so as to narrow the cross section, and provide for the flow of temperature control medium through the support pipe.

The insert element narrowing the cross section can also preferably have terminal flange connections which are connected releasably by means of a thread or preferably a bayonet closure and seal off the inner space of the support pipe.

A design is particularly preferred in which the insert element has a radial distributor for the heat transfer medium.

The insert element particularly preferably has a helical inner contour.

A further preferred design of the apparatus is characterized in that the support pipe (62) is closed at one end and has, at the other, open end of the support pipe, an insert element with inlet and outlet line for the heat transfer medium.

The insert element is particularly preferably in the form of a flanged pipe in which the heat transfer medium inlet line is connected to the pipe interior and the outlet is via the gap between insert element and support pipe.

In a preferred variant, an electrical resistance heating source, which is inserted into the support pipe (63), is arranged in the heat treatment reactor.

In a preferred embodiment, in order to improve the heat conductivity of the annular gap between heating source and support pipe, the annular gap is filled with a heat transfer medium.

A further preferred variant of the apparatus is characterized by a receiving vessel connected to the support pipe, for collection of the heat transfer fluid which displaced into the support pipe upon insertion or operation of the heating source.

In the area of its inlet and outlet, the heat treatment reactor particularly preferably has temperature sensors, e.g. PT100 platinum resistance sensors, for determining the heat transfer medium temperature and/or the product temperature.

A design of the apparatus is also particularly preferred in which the sensors are connected to flow regulators for the heat transfer medium stream and/or the product stream.

BRIEF DESCRIPTION OF THE DRAWINGS

FIG. 4 illustrates a UV irradiation reactor having a corrugated hose 5 over a UV-transparent support pipe 65, made of quartz glass, and UV emitter 25 installed in support pipe 65, with quartz windows 64 and UV sensors 26 & 27.

FIG. 4a illustrates an enlargement of the bottom part of the UV irradiation reactor of FIG. 4, showing distributor head 9 having an o-ring seal 33

EXAMPLES

Figure 1A:
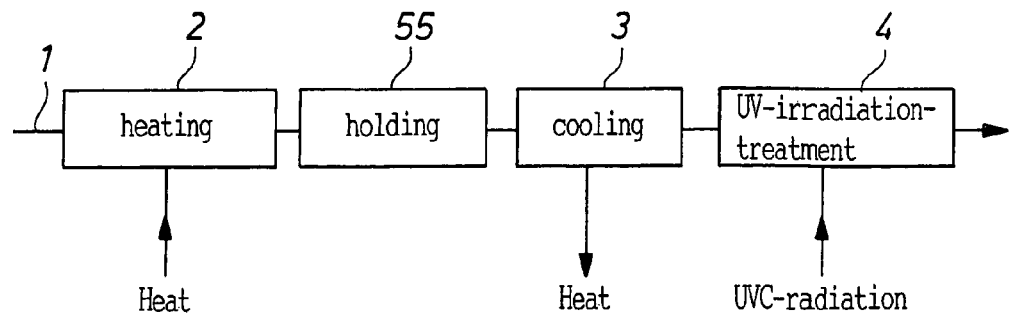
FIG. 1a illustrates a block diagram of the process of the invention, wherein the product is first subjected to the heat treatment step, then, following passage through the holding section is cooled and then subjected to the ultraviolet treatment step.
Figure 1B:
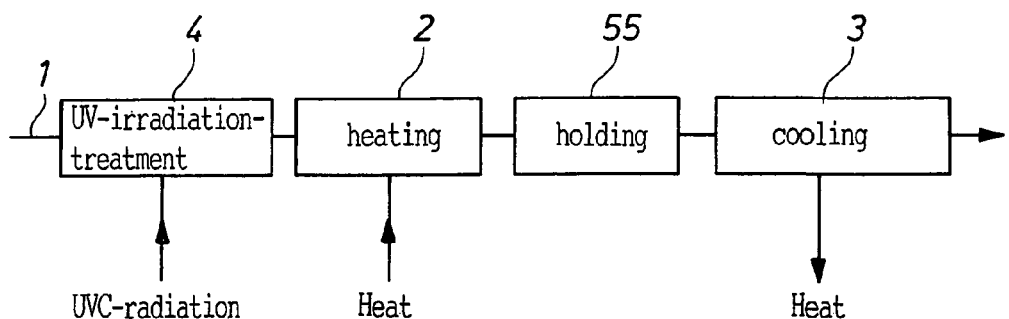
FIG. 1b illustrates a block diagram of the process of the present invention wherein the ultraviolet irradiation step is followed by the heat treatment step.
Figure 2:
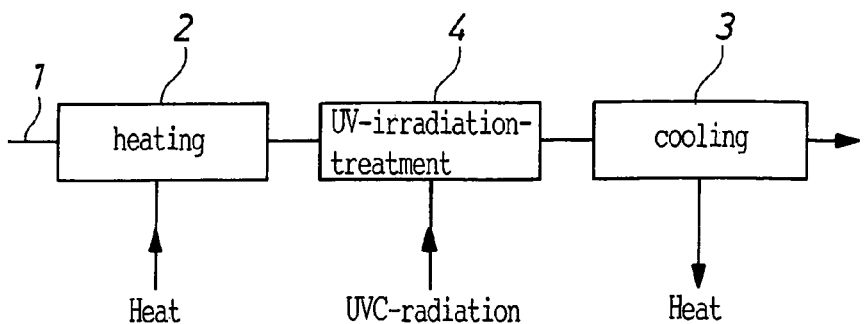
FIG. 2 illustrates a block diagram of the process of the present invention wherein the product is cooled immediately after the ultraviolet irradiation treatment, without first passing through a holding section.
Figure 3:
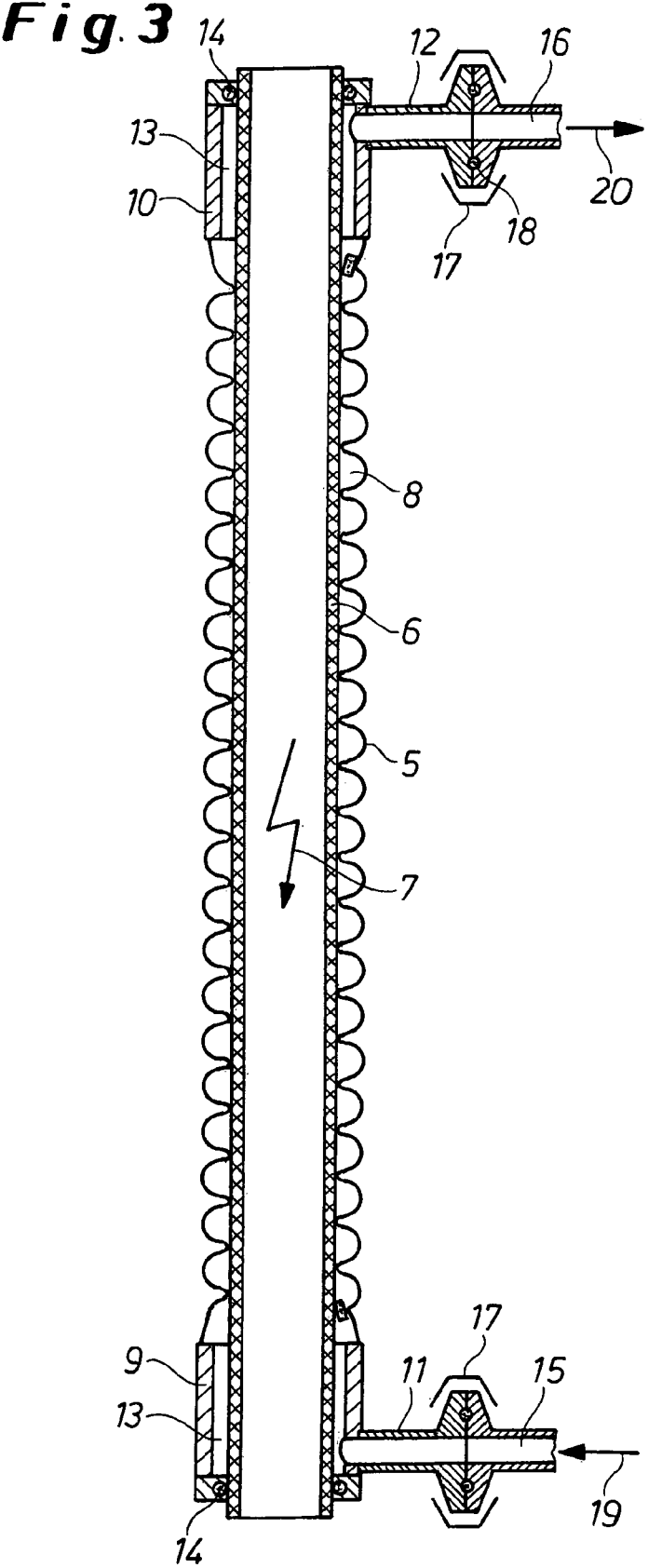
FIG. 3 illustrates a reactor with helical channels according to the invention.
Figure 3A:
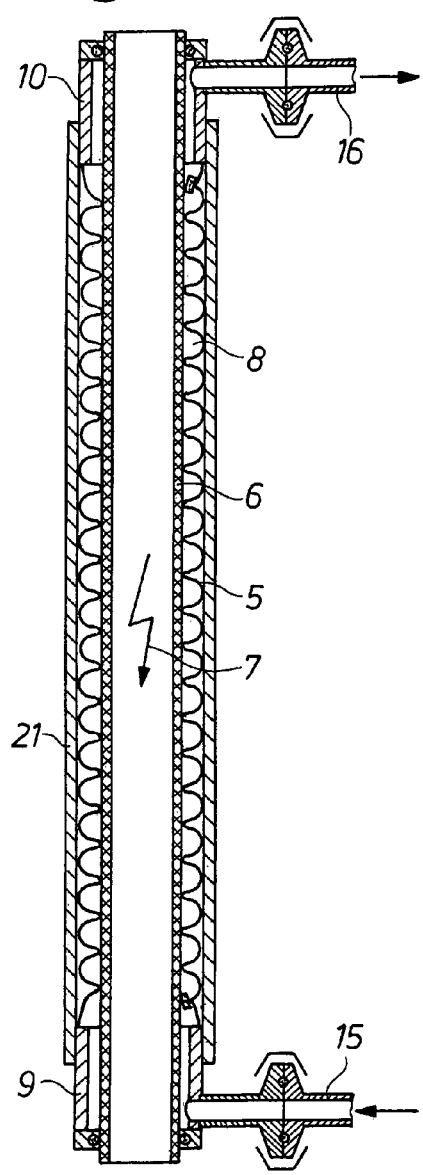
FIG. 3a illustrates a reactor according to the invention, having a sheath 21 over the corrugated hose forming the helical channels.
Figure 3B:
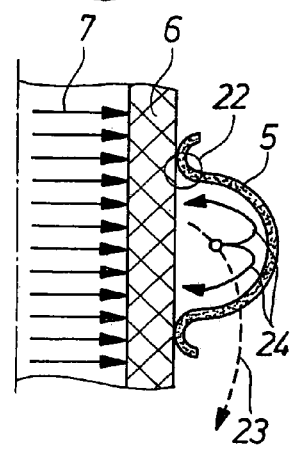
FIG. 3b illustrates a cross-section of a channel of the reactor, with contact point 22 enlarged.
Figure 3C:
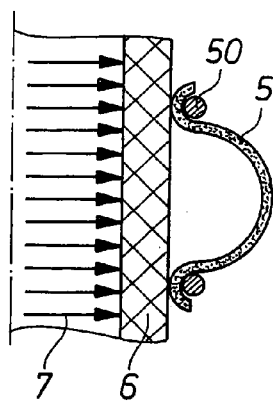
FIG. 3c illustrates a cross-section of a channel of the reactor, formed with a corrugated hose having metal reinforcements 50.

As is shown in FIGS. 3, 3a and 3b, reactors with helical channels (8) are used according to the invention as the apparatus for carrying out sterilization and virus inactivation. The channels are produced by drawing a helical hose (5) onto a cylindrical support body (6). By means of a suitable geometry of the corrugated hose (5), which has a slightly reduced internal diameter compared to the support body (6), a tight, force-fit connection between the two reactor elements is established. In this way, it is possible to prevent the axial short-circuit flows that would otherwise be caused by gaps between the flow channels, which, as tests confirm, would result in a considerable widening of the dwell time distribution. The product stream is expediently directed upwards in order to prevent back-mixing of the product stream through gas bubbles flowing in counter-current. Swelling of the corrugated hose (5) as a result of the pressure loss increasing in the case of larger product flows is undesirable because of the formation of short-circuit flows and is prevented, according to the invention, by a suitably dimensioned wall thickness of the corrugated hose (5) and/or by metal reinforcements inserted into the corrugated hose and/or by a sheath (21). The configuration of a jacket tube is in this case expediently such that the internal diameter of the jacket is slightly smaller than the external diameter of the hose, in order to generate an additional contact pressure without appreciable hose deformation. In the case of small pressure losses, a shrinkable tube easily fitted onto the corrugated hose can improve the pressure stability. Other jacket constructions which could likewise be used after module production could be made for example of half-shells and multiple wound layers of glass fiber-reinforced plastic.

The energy input takes place via the protective pipe (6) which, for UV treatment (see FIGS. 4 and 4a), is designed as a quartz pipe (65) transparent to UV rays, and, for thermal treatment (see FIGS. 5, 5a, 5b and 5c), is designed as a thin-walled metal pipe (34) with good heat conductivity. In both sterilization methods, coatings form on those surfaces of the support pipe used for energy input. These coatings referred to as fouling can be cleaned off where the soiling is able to be brought into contact with a cleaning agent. In this context, parts which prove particularly difficult to clean are the areas (22) particularly susceptible to fouling around contact points between hose and pipe (see FIG. 3b). Complete dismantling of the reactor, which is necessary in this case for carrying out cleaning in accordance with GMP, cannot be done on site by the operators because of the large amount of time needed and the high degree of precision. For this reason, according to the invention the reactors are supplied as disposable modules which are packaged under sterile conditions and are quick and easy to replace and are recommended for use in GMP sterilization processes.

After the sterile packaging has been opened, and immediately before the process starts, the reactors are installed by connecting the identical attachment pieces (11, 12) present on the distributor heads (9, 10) to the attachment pieces (15, 16) of the product line. So-called triclamp connections, consisting of the correspondingly shaped flange ends of the attachment pieces (11, 12, 15, 16), a connection clip (17) and a special seal (18), are particularly suitable for rapid and hygienic connection.

The distributor heads (9) and (10) are connected in mirror-symmetrical arrangement to the cylindrically widened ends of the corrugated hose. A completely hygienic connection is preferably guaranteed by means of an O-ring seal (33, see FIG. 4a). In the seal illustrated in FIG. 4a, the connection between hose (5) and O-ring (33) is obtained by pressing from outside by means of the ring (32). Other connection variants include welding the distributor heads to the corrugated hose, and integrating the distributor heads into the corrugated hose ends which have been modified by suitable, for example thermal, deformation. The distributor heads (9, 10) are sealed off with respect to the protective pipe (6, 65, 34) by means of O-rings (14).

In addition to supporting the reactor, the distributor heads (9, 10) have in particular the role of ensuring initial distribution of the product stream. The special design of the distributor heads ensures that it is possible to avoid any negative impact of the initial distribution on the dwell time characteristics. According to the invention, this is achieved by strictly limiting of the head volume contacted by the product, and this in turn by minimizing the gap width (28) and overall height (29). As dwell time studies show, by using distributor heads of minimized volume, it is generally possible to dispense with tangential delivery and discharge of the product stream in favor of a radial delivery which is preferable because of its easier and less costly production.

FIGS. 4 and 4a show the reactor provided for the UV irradiation. The support pipe (65) of the corrugated hose is made of UV-transparent quartz glass. One or more UV emitters (25) are installed in the centre of the support pipe (65) for UV treatment. To monitor fouling, the distributor heads (9) and (10) are equipped with quartz windows (64) through which it is possible for the UV sensors (26, 27) to measure the UV light emitted into the head space. According to the invention, the information provided by the sensors is used for GMP-compliant documentation of the irradiation procedure and for keeping the radiation dose constant by suitable adjustment of the product dwell time across the product throughput. In this way, the film formation (i.e., fouling) on the quartz glass and the loss of radiation capacity of the UV radiation source can be compensated for without affecting the irradiation procedure.

FIGS. 5, 5a, 5b, 5c, 6 and 7 show the reactors for sterilization by thermal treatment, which reactors can be used equally for heating and for cooling the product stream. The support pipe (34) is made of an FDA-approved material that is pressure-stable, very thin and has good heat transfer properties. For example, stainless steel pipes afford good heat transfer conditions. By electropolishing the pipe surface directed towards the product, it is possible to reduce the tendency towards formation of fouling layers on the heating surfaces.

For heat sterilization, the modules are connected via flange connections (36, 37, 42) and (46, 41, 42) to heating media, for example steam or hot water, or, for cooling purposes, to cooling media, for example cold water or brine. While the temperature control liquids expediently flow through the reactors in an upward direction in order to prevent formation of gas pockets, it is preferable, when using steam as temperature control medium, for the through-flow to be in a downward direction, for removal of condensate. To improve the heat transfer both for heating and cooling, particularly when using liquids as heat transfer media, it is generally necessary to increase the speed at which the media flow across the heat exchange surface (34) by providing inserts (35) which narrow the cross section.

Figure 5:
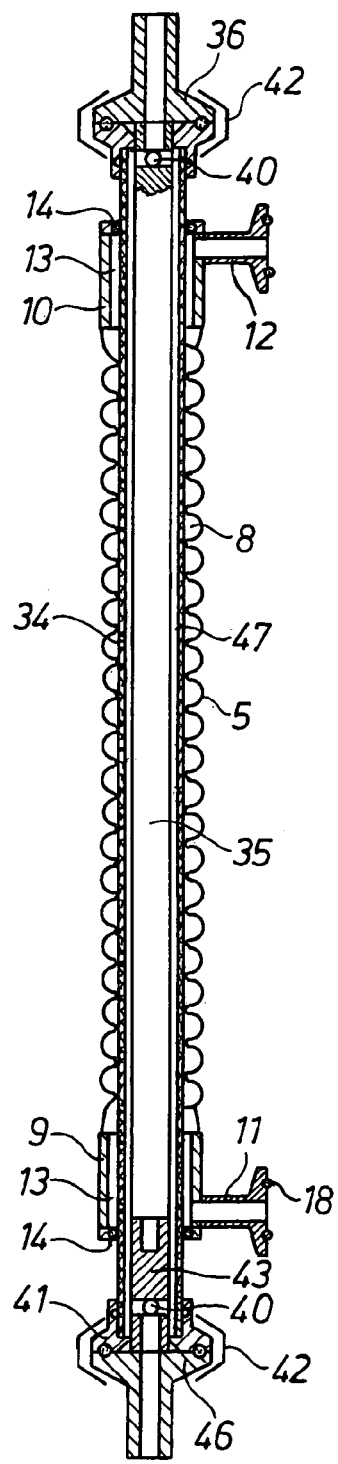
FIG. 5 illustrates a thermal treatment reactor according to the invention, having support pipe 34 formed of a heat-transmitting material with flange connections 36, 46 for heat transfer media.
Figure 5A:
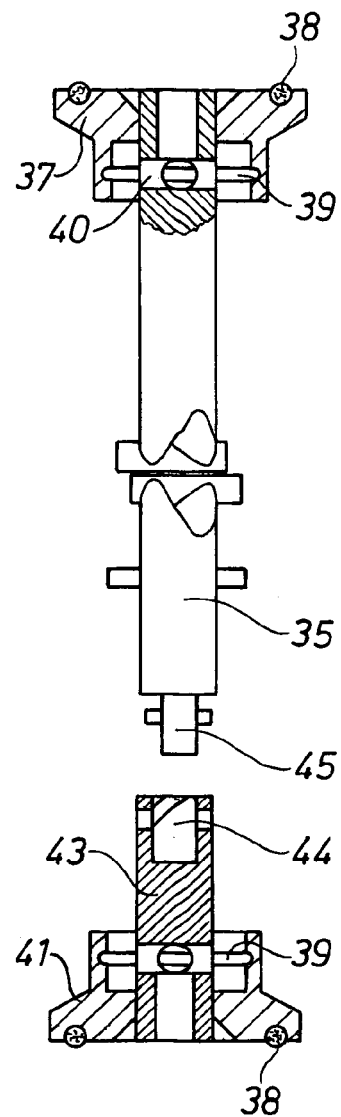
FIG. 5a illustrates an insert made of a two part cylinder 35, 43, the parts of which can be connected to each other with a force fit by a bayonet closure 44, 45.
Figure 5B:
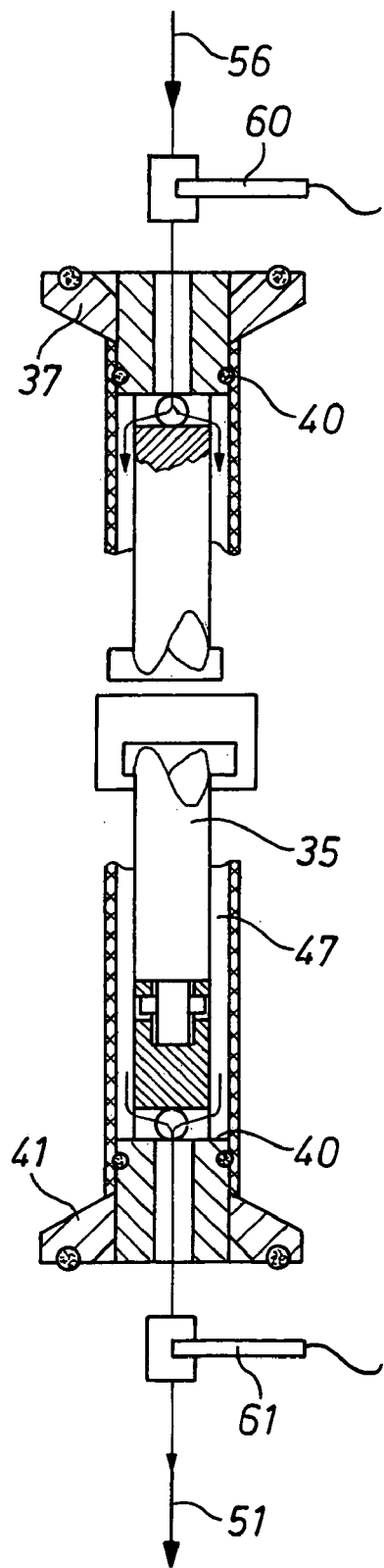
FIG. 5b illustrates a cutaway of a reactor having the insert of FIG. 5a with the two parts connected to each other
Figure 5C:
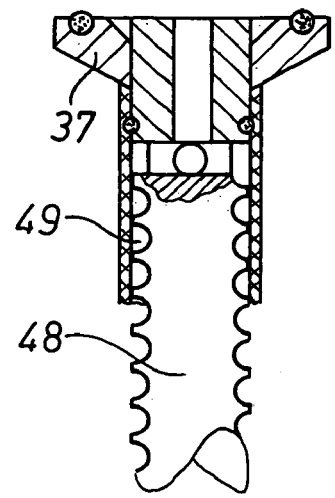
FIG. 5c illustrates an insert element 48, which when inserted into the support pipe of the thermal treatment reactor of the invention forces the heat transfer media to follow a helical path 49.

As FIGS. 5, 5a and 5b show, such an insert can be made up of a two part cylinder (35, 43) welded to the connection flanges (37, 41). The two cylinder elements (35, 43) can be connected to one another with a force fit by means of a thread or, in order to reduce the load on the O-ring during assembly, more preferably by means of a bayonet closure (44, 45). The centrally delivered heat transfer media (56, 51) are distributed via the radial bores (40) into the annular gap (47) between insert (35, 43) and support pipe (34) and are removed again at the opposite end via the bores (40) which are in a mirror-symmetrical arrangement. As FIG. 5c shows, instead of the cylindrical annular gap, it is possible for the insert element (48), in this case set closer to the wall of the support pipe, to be shaped in such a way as to force the temperature medium to follow a helical flow path (49) which, because of the secondary flows which arise, provides an additional contribution to improving the heat exchange.

Figure 6:
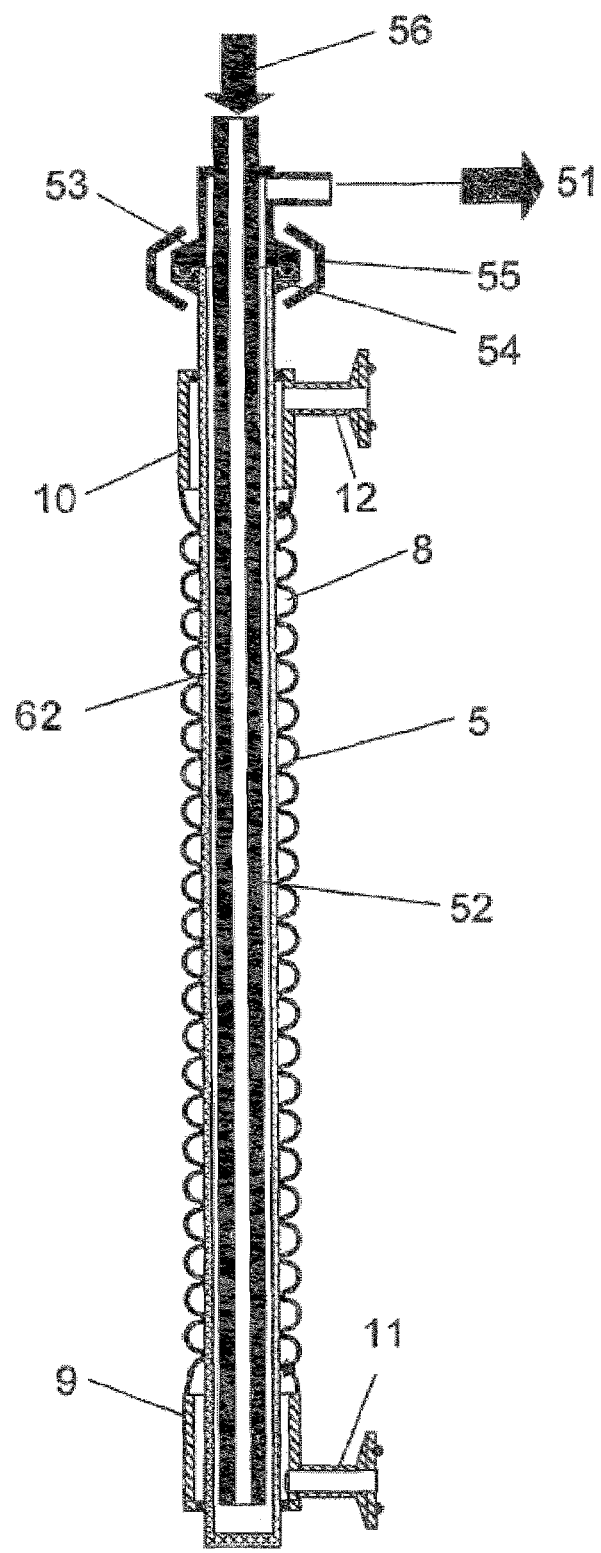
FIG. 6 illustrates a thermal treatment reactor of the invention having a lance 52 through which heat transfer media can be conveyed to a closed end of support pipe 62, whereby the heat transfer media will then be introduced into the annular gap 47 to flow back up to outlet 51.

In the reactor shown in FIG. 6, the liquid heat transfer media are conveyed through a lance (52) to the closed opposite end of the support pipe (62), where these media are introduced into the annular gap (47) through which they flow in the opposite direction. The handling of the temperature control modules is considerably simplified in this way because, as a result of the flange (53) which can be integrated into the module, it is possible to dispense with the pre-assembly of the flange ends (37, 41) on the support pipe (34), as shown in FIG. 5. In addition, by moving the delivery and removal points of the temperature control media to the same end, the assembly work involved for installation in the production plant is reduced to securing a single flange connection (53, 54, 42). In the case of heat transfer media in the form of steam, the flow direction is reversed for condensate removal, so that the steam is first introduced into the annular gap (47) and flows downward through the latter before being flowing upwards, together with the condensate, through the lance (52). To avoid problems by having some condensate residing at the bottom, the bottom area is preferably either connected to a condensate drain or equipped with a demisting system.

Figure 7:
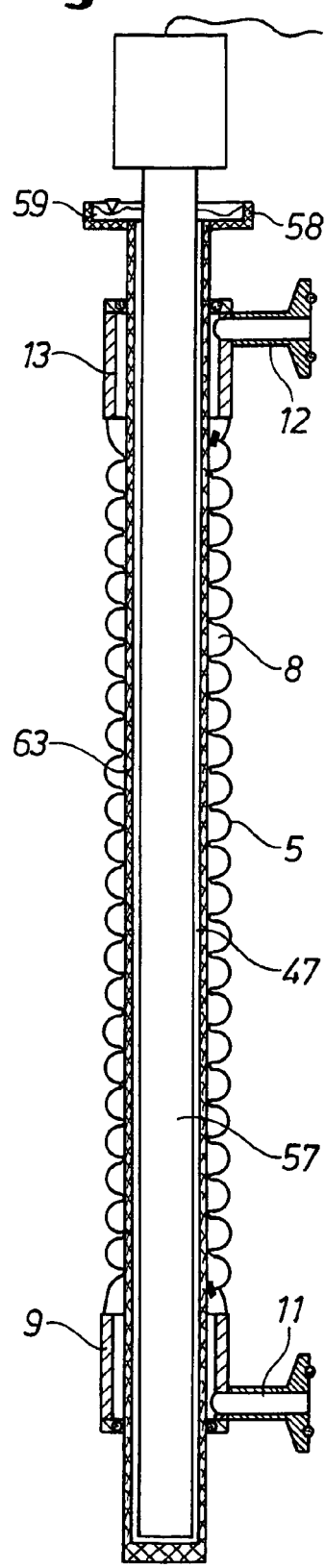
FIG. 7 illustrates the heat treatment reactor of the invention having an electrical heating source 57.

In the arrangement shown in FIG. 7, indirect heating via flowing heat transfer media has been replaced by direct electrical heating via a cylindrical heating source (57). For this purpose, the heating source (57) is inserted into the support pipe (63) closed off at the opposite end. The poor heat transfer properties found even in the case of thin air-filled annular gaps (47) between heating source (57) and support pipe (63) can be avoided by filling with special heat transfer media (59). When using liquid heat transfer media in the vertically positioned support pipe, the liquid displaced upon insertion of the heating source (57) can be collected in the receiving vessel (58) connected to the support pipe.

INDEX LIST TO THE REFERENCES IN THE DRAWINGS 1 fluid media
2 heating
3 cooling
4 UV irradiation treatment
5 corrugated helical hose
6 cylindrical support body
7 irradiation or heating source
8 helical channel
9/10 distributor heads
11/12 attachment pieces
13 annular gap
14 O-ring
15/16 attachment pieces
17 connection clip
18 seal
19 fluid media inlet
20 fluid media outlet
21 sheath
22 contact point
23 primary flow direction
24 secondary flow
25 UV emitter
26/27 UV sensors
28 gap width
29 overall height
30 window
31 O-ring seal
32 connection ring
33 O-ring seal
34 thin-walled metal pipe (heat transmitting)
35 two part cylinder insert (top)
36/37 flange connection
38 O-ring
39 O-ring seal
40 radial bores
41 flange connection
42 connection clamp
43 two part cylinder insert (bottom)
44 bayonet closure (bottom)
45 bayonet closure (top)
46 flange connection
47 annular gap
48 insert element
49 helical flow path
50 metal reinforcements
51 heat transfer media outlet
52 lance
53/54 connection flange
55 holding
56 heat transfer media inlet
57 electrical heating source
58 receiving vessel
59 special heat transfer media
60/61 temperature sensors
62/63 support pipe
64 (quartz) windows
65 UV-transparent quartz pipe

We claim:

1. A continuous process for sterilization and, optionally, virus inactivation of fluid media, comprising the steps of heating said fluid media to a temperature of 40° to 135° C. and irradiating said fluid media with UV irradiation at an irradiation density of 5 to 300 W/m$^2$;

and cooling the heated fluid media, wherein said heating and cooling steps take place independently of one another and within 0.1 to 10 seconds of each other.

2. The process according to claim 1, wherein said fluid media is held at said temperature for up to 50 seconds.

3. The process according to claim 1, wherein said heating and cooling is performed in successive steps of heating, temperature holding, and cooling, and the UV irradiation is performed before, after or during one or more of said successive steps.

4. The process according to claim 3, wherein one or more of said successive steps are carried out in disposable reactors which are pre-sterilized and cleaned according to GMP.

5. The process according to claim 1, wherein the heating is carried out with a high-performance heat exchanger having a thermal conductivity of k>1000 W/m$^2$*K.

6. The process of claim 1, wherein said fluid media is selected from the group consisting of foodstuffs, milk products, fruit juice products, chemical or pharmaceutical products, viral vaccines, active substance or proteins produced by genetic engineering, active substances or proteins from transgenic animals or plants, and blood plasma, or products obtained from blood plasma.

7. An apparatus for sterilization and, optionally, virus inactivation of fluid media, by a combined application of a heat treatment and UV irradiation treatment, comprising at least a heat treatment reactor, with an optional temperature holding section, a UV irradiation reactor and a cooling reactor, wherein at least the heat treatment reactor and the UV irradiation reactor each comprise a sterilization and/or inactivation chamber for through-flow of the fluid media, which chambers are formed of a deformable, helical, profiled hollow cylinder which is drawn tight onto the wall of a rigid, straight, cylindrical support body, the cylindrical support body of the chamber of the heat treatment reactor being of a heat conductive material and the cylindrical support body of the chamber of the UV irradiation reactor being transparent to ultra violet irradiation.

8. Apparatus according to claim 7, wherein said deformable, helical hollow cylinder is a corrugated plastic hose which is connected at both ends to distributor heads for delivery and discharge of said fluid media.

9. Apparatus according to claim 8, wherein said distributor heads have tangential or radial product delivery and discharge lines, free of dead space, in an annular gap between distributor head and support pipe.

10. Apparatus according to claim 8, wherein the distributor heads are worked from the hose ends by thermal deformation of the corrugated hose or are made from a plastic material produced and worked by injection-molding or stretching, or by a combination of injection molding and stretching, and are connected with a force fit to the hose ends which are cylindrically widened, with an O-ring connection pressed on from the outside.

11. Apparatus according to claim 8, wherein said corrugated hose has an outer jacket or a reinforcement.

12. Apparatus according to claim 11, wherein said outer jacket is formed by a shrinkable plastic tube, a pipe pushed over the plastic hose, or a two-part cylindrical shell, and said reinforcement is formed of a steel or plastic coil.

13. Apparatus according to claim 11, wherein said outer jacket is formed by a shrinkable plastic tube, a pipe pushed over the plastic hose, or a two-part cylindrical shell, and said reinforcement is formed of a steel or plastic coil.

14. Apparatus according to claim 7, wherein said UV reactor comprises one or more UV emitters as energy source in the cylindrical support body, and the cylindrical support body is made of a material transparent to UV light, and optionally has a corrugated plastic hose as said deformable helical profiled hollow cylinder.

15. Apparatus according to claim 7, further comprising windows formed in the distributor heads and sealed in the distributor heads via an O-ring connection, for observing the UV energy radiated into the fluid media.

16. Apparatus according to claim 15, further comprising UV sensors built into the distributor heads for detecting the UV radiation intensity radiated into the fluid media.

17. Apparatus according to claim 7, wherein said heat treatment reactor comprises a pipe formed of heat transmitting material as the cylindrical support body, and a corrugated hose made of plastic as said deformable helical profiled hollow cylinder.

18. Apparatus according to claim 7, further comprising an insert element incorporated in the centre of the support pipe of the heat treatment reactor to narrow the cross section for heat transfer fluid flow through the cylindrical support body.

19. Apparatus according to claim 18, wherein said insert element has terminal flange connections which are connected releasably by a thread or a bayonet closure and seal off the inner space of the support pipe.

20. Apparatus according to claim 19, wherein said insert element has a radial distributor for heat transfer fluid.

21. Apparatus according to claim 18, wherein the insert element has a helical inner contour.

22. Apparatus according to claim 7, wherein said heat treatment reactor comprises a support pipe which is closed at one end and is open at the other end and has, at said other, open end, an insert element with inlet and outlet for heat transfer fluid.

23. Apparatus according to claim 22, wherein the insert element is comprised of a flanged pipe in which an inlet line is connected to the pipe interior and an outlet line is connected to a gap between the insert element and the support pipe.

24. Apparatus according to claim 7, wherein said heat treatment reactor comprises an electrical resistance heating source, which is inserted into a support pipe.

25. Apparatus according to claim 24, further comprising an annular gap between said heating source and said support pipe, which annular gap is filled with a heat transfer medium.

26. Apparatus according to claim 25, further comprising a receiving vessel connected to the support pipe adapted to receive heat transfer fluid displaced upon insertion of heat source into said support pipe, or upon operation of said heat source.

27. Apparatus according to claim 7, wherein said heat treatment reactor comprises an inlet and an outlet having temperature sensors for temperature determination of the heat transfer media, temperature of the fluid media, or the heat transfer media temperature and the fluid media temperature.

28. Apparatus according to claim 27, wherein said sensors are connected to flow regulators for the heat transfer medium stream, the fluid media or the heat transfer medium stream and the fluid media stream.

* * * * *